United States Patent [19]
Bowe et al.

[11] Patent Number: 6,150,302
[45] Date of Patent: Nov. 21, 2000

[54] USE OF A SEMICARBAZONE PLANT GROWTH REGULATOR FOR CROP YIELD ENHANCEMENTS

[75] Inventors: Steven J. Bowe, Hockenheim; Wilhem Rademacher, Linburgerhof, both of Germany; Larry J. Newsom, Greenville, Miss.; Gregory P. Ferguson, Conway, Ark.

[73] Assignee: BASF Corporation, Mount Olive, N.J.

[21] Appl. No.: 09/461,352

[22] Filed: Dec. 15, 1999

[51] Int. Cl.$^7$ .................................................. A01N 43/40
[52] U.S. Cl. ................................................. 504/244
[58] Field of Search .............................. 504/244

[56] References Cited

U.S. PATENT DOCUMENTS

| | | | |
|---|---|---|---|
| 4,272,280 | 6/1981 | Hedrich | 71/88 |
| 4,462,821 | 7/1984 | Rutter et al. | 71/99 |

*Primary Examiner*—Shelley A. Dodson
*Assistant Examiner*—Alton Pryor
*Attorney, Agent, or Firm*—Nixon & Vanderhye P.C.

[57] ABSTRACT

Fruit yield enhancement is achieved by applying a semicarbazone in a fruit yield enhancing effective amount to the locus of a fruit bearing plant. Most preferably, the semicarbazone treatment is practiced at the onset of reproductive growth—that is, at the onset of the flowering and/or fruit reproductive growth stage of the plant. Most preferably, the semicarbazone is diflufenzopyr.

8 Claims, No Drawings

6,150,302

USE OF A SEMICARBAZONE PLANT GROWTH REGULATOR FOR CROP YIELD ENHANCEMENTS

FIELD OF THE INVENTION

The present invention relates to the use of a semicarbazone plant growth regulator for crop yield enhancements.

BACKGROUND AND SUMMARY OF THE INVENTION

Crop yield is subject to many factors including crop genetics, environment (e.g., air, soil and/or water) and cultural conditions. These factors must be optimal in order to realize maximum yield potential for growing crop plants. Crop plants whose fruit is the harvested commodity seem to be especially sensitive to stress factors which limit yield. Less than ideal conditions or "stress" may lead to smaller fruit size, limited fruit formation and/or fruit abortion which results in a net loss of yield.

Plant growth regulators (PGR's) affect the physiology of plant growth and influence the natural rhythm of a plant. More specifically, plant growth regulators may, for example, reduce plant height, stimulate seed germination, induce flowering, darken leaf coloring, minimize lodging of cereals, slow grass growth on lawns, reduce boll rot and provide better boll retention in cotton.

Diflufenzopyr (DFFP), a semicarbazone PGR, has been found to enhance the marketable yield of fruiting crops by increasing the harvested size and/or number of fruits retained by the crop. DFFP may thus also reduce the dominance of older fruits over younger fruits ("primigen dominance") resulting in enhanced fruit set and yield.

The yield enhancements achieved by the present invention may usefully be employed with crops that are especially sensitive to stress factors (e.g., cotton, tomatoes or the like) or which poorly regulate fruit load due to determinant growth (e.g., some soybean varieties), or so-called "alternate year" fruit producers (e.g., apples, pears, peaches, apricots, pistachios and the like).

Broadly, therefore, the present invention is directed toward the fruit yield enhancement by applying a semicarbazone in a fruit yield enhancing effective amount to the locus of a fruit bearing plant. Most preferably, the semicarbazone treatment is practiced at the onset of reproductive growth—that is, at the onset of the flowering and/or fruit reproductive growth stage of the plant. Most preferably, the semicarbazone is diflufenzopyr. By using such an early treatment strategy, improvements in the plant's fruit yield are achieved.

These and other aspects and advantages of the present invention will become more clear after careful consideration is given to the following detailed description of the preferred exemplary embodiments thereof.

DETAILED DESCRIPTION OF THE INVENTION

The present invention can be employed with crop plants which display determinate or indeterminate growth patterns. Determinate plants have a defined period of vegetative growth followed by a defined interval of reproductive growth in which there is a maximum number of flowers initiated per plant. An indeterminate plant growth pattern, on the other hand, is characterized by an initial period of vegetative growth followed by a period where both vegetative and reproductive growth occur together. The length of the second period and the number of flowers produced are determined largely by the growing conditions.

One example of an important crop plant that displays an indeterminate growth pattern is cotton (*Gossypium hirsutum*). Cotton is a perennial of tropical origin that is cultivated as an annual in agricultural production in temperate and subtropical regions of the world. After an initial period of vegetative growth, a cotton plant initiates reproductive growth while vegetative growth continues. Flower buds (squares) appear and develop into flowers and after pollination give rise to fruit that are referred to as bolls.

Due to its indeterminate nature, squares continue to appear long after there is sufficient time left in the growing season for these squares to develop into mature, harvestable bolls. The growth and development of these late squares and young bolls drains the limited resources of the plant that might be better utilized by bolls that have sufficient time to mature to a harvestable stage. Likewise, the shoot of the cotton plant continues to grow and initiate new leaves throughout most of the growing season. Many of the leaves that are initiated late in the growing season will never become carbohydrate source leaves due to insufficient time remaining in the growing season. Thus, these young leaves demand a portion of the carbohydrates and other nutrients that could be better utilized by the bolls that are likely to be harvested.

DFFP may also reduce shedding of older fruit when plants are subjected to stress factors, including drought or insects, for example.

An example of an important crop plant which may exhibit both a determinate and indeterminate growth patterns is the soybean plant (*Glycine max*).

The preferred plant growth regulator that is employed in accordance with the present invention includes substituted semicarbazones and related compounds, such as thiosemicarbazones and isothiosemicarbzones and salts thereof, as described more fully in U.S. Pat. Nos. 5,098,462 and 5,098,466 (the entire content of each U.S. patent being expressly incorporated hereinto by reference). These compounds may be synthesized by reacting a carbonyl compound and a semicarbazide or thiosemicarbazide together at room temperature in the presence of an alcohol solvent, such as methanol or ethanol and with or without an acid catalyst to give the semicarbazones that may be employed in the practice of the present invention. The most preferred semicarbazone employed in the practice of this invention is diflufenzopyr.

The semicarbazone is applied to the locus of the plant in an amount between about 0.01 to about 5.0 grams of active ingredient per hectare (g ai/ha), and particularly between about 0.05 to about 1.0 g ai/ha.

The semicarbazone is applied in accordance with the present invention early in the reproductive cycle of the plant. That is, the semicarbazone is applied at the onset of the fruit and/or flowering reproductive growth stage of the plant. By onset of the fruit and/or flowering reproductive growth stage is meant that growth stage of the plant which begins prior to flower bud growth (i.e., bud swell, square formation) and continues through pollination or fruit set.

The semicarbazones may be applied in the form of dusts, granules, solutions, emulsions, wettable powders, flowables and suspensions. Application of a compound as an active ingredient is made according to conventional procedure to the locus of the plant in need of the same using the appropriate amount of the compound per acre as will be described below. According to the present invention the application of the compound to the "locus" of the plant includes application to the plant or parts of the plant.

The semicarbazone compound may be applied to above ground portions of the plants. The application of liquid and particulate solid plant growth regulator compositions to above ground portions of plants may be carried out by conventional methods, for example, boom and hand application, including sprayers or dusters. The composition may be applied aerially as a spray, if desired. The semicarbazone compound employed in the practice of the present invention is most preferably used in the form of aqueous solutions. The solutions may be applied in a conventional manner, for example, by spraying, atomizing or watering the locus of the plant.

The semicarbazone compound may also be applied in conjunction with other ingredients or adjuvants commonly employed in the art. Examples of such ingredients include drift control agents, defoaming agents, preservatives, surfactants, fertilizers, phytotoxicants, herbicides, insecticides, fungicides, wetting agents, adherents, nematocides, bactericides, trace elements, synergists, antidotes, mixtures thereof and other such adjuvants and ingredients well known in the plant growth regulating art.

Regardless of the manner in which it is applied, the semicarbazone is applied to the locus of a crop plant in need of yield enhancement in an amount between about 0.01 to about 5.0 g ai/ha, and particularly between about 0.;05 to about 1.0 g ai/ha.

The present invention will be further illustrated by way of the following non-limiting examples.

EXAMPLE 1

Trials were conducted over several different growing seasons as shown in Table I below by applying a single or sequential application of DFFP at rates of 1 g ai/ha or less to the locus of growing cotton plants at the onset of production (i.e., pinhead square, or PHS). All applications utilized a spray adjuvant (typically 0.25% NIS or 0.625% v/v Dash® HC).

As is evident in the data of Table I, average yield increases over all the trials of 104% to 105% were achieved as compared to the untreated plants. Furthermore, it was observed that application of DFFP tended to increase plant yields when growing conditions were poorer.

EXAMPLE 2

A trial under controlled field-like conditions with determinate soybeans was conducted using DFFP application rates of 0.1 to 3 grams ae/ha at 30% bloom. The yield increased between 107–110% as compared to the untreated control plants. Sequential application of DFFP at a rate of 0.1 to 3 g ae/ha at 30% bloom and at initial pod formation increased yield 105–107% as compared to the untreated control.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for improving plant fruit yield comprising applying to a locus of the plant at onset of flowering or fruit growth, a fruit yield improving effective amount between about 0.01 to about 5.0 g ai/ha of a diflufenzopyr plant growth regulator.

2. The method of claim 1, wherein the application rate of diflufenzopyr is between about 0.05 to about 1.0 g ai/ha.

3. The method of claim 1, wherein the semicarbazone is applied together with at least one adjuvant.

4. The method of claim 1, wherein the semicarbazone is applied in the form of a liquid or a solid particulate.

5. The method of claim 1, wherein the plant is a cotton or soybean plant.

TABLE I

Seed Cotton Yield - Percent of Untreated Check

| Treatment | Rate[1] | Timing | Trial Years (n)[2] | | | | | Averages | |
| | | | 1 (1) | 2 (5) | 3 (1) | 4 (6) | 5 (2) | Years 4 & 5 (8) | Years 1–5 (15) |
|---|---|---|---|---|---|---|---|---|---|
| Comp 1 (Untreated) | — | — | 100% | 100% | 100% | 100% | 100% | 100% | 100% |
| Comp 2 (PGR IV)[3] | 0.875 | | | | | 97% | 104% | 99% | |
| DFFP | 0.1 | PHS | 95% | 104% | 131% | 104% | 108% | 105% | 105 |
| DFFP | 0.1 | PHS + 2 wks | | | | 103% | 102% | 103% | |
| DFFP | 0.1 | 1st Bloom | | | | 102% | 96% | 100% | |
| DFFP | 0.5 | PHS | 106% | 98% | 122% | 104% | 98% | 103% | 104 |
| DFFP | 0.5 | PHS + 2 wks | | | | 102% | 100% | 102% | |
| DFFP | 0.5 | 1st Bloom | | | | 103% | 97% | 102% | |
| DFFP | 1.0 | PHS | 112% | 93% | | 102% | 100% | 101% | 100 |
| DFFP | 1.0 | PHS + 2 wks | | | | 100% | 102% | 101% | |
| DFFP | 1.0 | 1st Bloom | | | | 95% | 100% | 96% | |
| DFFP | 0.1 | (note 4) | | | | 100% | 101% | 100% | |
| DFFP | 0.1 | (note 4) | | | | | 114% | 114% | |

Notes:
(1) All rates for DFFP are expressed as grams ai/ha; PGR IV rate expressed as liters/ha
(2) Rates for Trial Years 2 and 3 are rounded for inclusion in summary
(3) PGR IV = indolbutic acid and gibberellic acid (Microflow Co., Lakeland, FL)
(4) 2lf + PHS + 1st Bloom 6. A method for improving boll yield of a cotton plant comprising applying to a locus of the cotton plant from the onset of pinhead square stage through boll formation, a boll yield enhancing effective amount of a diflufenzopyr plant growth regulator.

7. The method of claim 6, wherein the application rate of diflufenzopyr is between about 0.01 to about 5.0 g ai/ha.

8. The method of claim 6, wherein the application rate of diflufenzopyr is between about 0.05 to about 1.0 g ai/ha.

* * * * *